United States Patent [19]

Oxenrider et al.

[11] 4,140,717

[45] Feb. 20, 1979

[54] PROCESS FOR HALOGENATING α,α-DIALKOXYALKYL KETOXIMES

[75] Inventors: Bryce C. Oxenrider, Florham Park; Milorad Rogic, Whippany, both of N.J.

[73] Assignee: Allied Chemical Corporation, Morris Township, Morris County, N.J.

[21] Appl. No.: 830,234

[22] Filed: Sep. 2, 1977

[51] Int. Cl.$^2$ .................. C07C 131/04; C07C 131/02; C07C 131/00
[52] U.S. Cl. ................................ 260/566 A; 562/562
[58] Field of Search ...................................... 260/566 A

[56] References Cited

U.S. PATENT DOCUMENTS 3,517,047  6/1970  Ohno et al. ...................... 260/566 A
3,928,445  12/1975  Rogic et al. ...................... 260/566 A

OTHER PUBLICATIONS

Angew. Chem. Internat. Edit., vol. 7, pp. 387–388 (1968).

*Primary Examiner*—Gerald A. Schwartz
*Attorney, Agent, or Firm*—Robert J. North; Robert A. Harman

[57] ABSTRACT

A process is described for directly mono-brominating or mono-chlorinating α,α-dialkoxyalkyl or α,α-dialkoxycycloalkyl ketoximes in the β-position. Particularly described is the direct chlorination of 2,2-dimethoxycyclohexanone oxime to produce 3-chloro-2,2-dimethoxycyclohexanone oxime, a useful intermediate in the preparation of L-lysine.

13 Claims, No Drawings

PROCESS FOR HALOGENATING α,α-DIALKOXYALKYL KETOXIMES

BACKGROUND OF THE INVENTION

1. Field of the Invention

This invention relates to a process for directly mono-brominating or mono-chlorinating α,α-dialkoxyalkyl or α,α-dialkoxycycloalkyl ketoximes in the β-position and particularly the production of 3-chloro-2,2-dimethoxycyclohexanone oxime, a useful intermediate in the synthesis of L-lysine.

1. Brief Description of the Prior Art

L-lysine is one of the essential amino acids required in the metabolism of all animals. Since many animal bodies are incapable of producing this required nutritive factor, it must be supplied from an external source such as by the animal and vegetable proteins of a normal diet. Due to the cost and restricted availability of these natural animal and vegetable sources of proteins, synthetic methods for the production of L-lysine are being investigated. Synthetic L-lysine could be used as a supplement in animal diets, particularly in the diets of poultry and swine. Thus, there is a need for an inexpensive, facile and efficient route for the production of synthetic L-lysine.

A synthesis of 3-chloro-2,2-dimethoxycyclohexanone oxime is described in U.S. Pat. No. 3,928,445 (1975), involving the chlorination of 2-alkoxy-3-oximinocyclohexenes and particularly, 2-methoxy-3-oximinocyclohexene. However, the 2-methoxy-3-oximinocyclohexene is a relatively expensive intermediate, and would represent a significant cost factor in a synthesis of L-lysine based on this intermediate.

Chlorination of cyclohexanone oxime with alkyl hypochlorites leads to 1-nitroso-1-chlorocyclohexane and is described in Angew. Chem. internat. Edit., Vol. 7 (1968), pp. 387-88.

The use of a large excess of chlorine leads to chlorinated pyridine derivatives and is described in U.S. Pat. No. 3,830,820 (1974).

U.S. Pat. No. 3,517,047 (Ohno and Naruse, 1970) describes the chlorination of 2-alkoxycycloalkylketone oximes in the presence of trivalent phosphine to form 1-chloro-1-nitroso-2-alkoxycycloalkanes which are intermediates in the synthesis of linear aliphatic omegacyanoaldehydes. However, the chlorination process does not directly produce 3-chloro-2-alkoxycycloalkyl ketoximes.

What is needed and what the prior art does not provide is an inexpensive synthetic route for directly mono-brominating or mono-chlorinating α,α-dialkoxyalkyl and α,α-dialkoxycycloalkyl ketoximes in the β-position.

SUMMARY OF THE INVENTION

In accordance with the present invention there is provided a process for mono-brominating or mono-chlorinating an α,α-dialkoxyalkyl or α,α-dialkoxycycloalkyl ketoxime in the β-position comprising contacting a solution of such ketoxime selected from the following formulae:

$$\begin{array}{c}\text{NOH}\\\parallel\quad\alpha\quad\beta\\\text{R—C——C——CH}_2\text{—R'}\\/\;\backslash\\\text{OY}\quad\text{OZ}\end{array} \quad (A)$$

where

Y and Z of the alkoxy groups are independently selected from linear or branched $C_1$–$C_4$ alkyl; and R and R' are independently selected from linear or branched alkyl containing at least one carbon atom; or

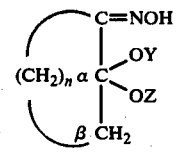

(B)

where

Y and Z of the alkoxy groups are independently selected from linear or branched $C_1$–$C_4$ alkyl and n is an integer of at least 2; or such compound substituted in the methylene $(CH_2)_n$ chain by at least one linear or branched $C_1$–$C_4$ alkyl radical; in an inert organic solvent with a chlorinating or brominating agent in a ratio of about 0.05 to 1.5 moles of chlorinating or brominating agent per mole of said ketoxime, in the presence of an acid catalyst, at a temperature above 0° C.

There is also provided a specific embodiment of the process for producing 3-chloro-2,2-dimethoxycyclohexanone oxime by contacting 2,2-dimethoxycyclohexanone oxime with a chlorinating agent.

DETAILED DESCRIPTION OF THE INVENTION AND THE PREFERRED EMBODIMENTS

The process of this invention is useful in preparing β-bromo- or β-chloro-α,α-dialkoxyalkyl or α,α-dialkoxycycloalkyl ketoximes from the direct bromination of chlorination of α,α-dialkoxyalkyl or α,α-dialkoxycycloalkyl ketoximes and can be illustrated by the following equations:

$$\begin{array}{c}\text{NOH}\\\parallel\;\alpha\;\;\beta\\\text{R—C—C—CH}_2\text{—R'}\\/\;\backslash\\\text{OY}\;\;\text{OZ}\end{array} \xrightarrow{\text{halogenating agent}} \begin{array}{c}\text{NOH}\;\;\text{X}\\\parallel\;\;\;\;|\\\text{R—C—C—CH—R'}\\/\;\backslash\\\text{OY}\;\;\text{OZ}\end{array} \quad (1)$$

(A)

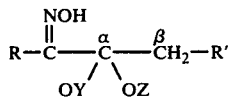 $\xrightarrow{\text{halogenating agent}}$ (2)

(B)

where

Y and Z of the alkoxy groups in the β-position are independently selected from linear or branched alkyl; R' and R' are independently selected from linear or branched alkyl containing at least one carbon atom and n is an integer of at least 2; and x in the β-position is either bromine or chlorine, and the methylene $(CH_2)_n$ chain can be substituted with one or more linear or branched $C_1$–$C_4$ radicals.

The halogenating agents referred to in the above equations are conventional chlorinating or brominating agents such as chlorine, bromine and the like. The term "ketoxime" as used hereinafter is meant to denote an α,α-dialkoxyalkyl or α,α-dialkoxycycloalkyl ketoxime.

It has been suprisingly found the ketoximes of formula A and B can be directly mono-chlorinated or mono-brominated in the beta (β) position by the process of this invention as indicated in the absence of the "normal" halogenated products, as is known in the prior art, of (a) 1-nitroso-1-chloro or 1-nitroso-1-bromo derivatives or (b) chlroinated pyridine derivatives. The process also possesses the advantage of eliminating the necessity of using starting 2-alkoxy-3-oximino-cyclohexenes for producing the β-chloro or β-bromo ketoxime, as required in U.S. Pat. No. 3,928,445, supra.

The process of this invention conveniently yields the β-bromo or β-chloro-substituted ketoximes in high yields in essentially a one "pot", one step reaction, thereby eliminating additional process steps as required in U.S. Pat. No. 3,928,445.

A particular embodiment of the invention is the production of 3-chloro-2,2-dimethoxycyclohexanone oxime (II) directly from 2,2-dimethoxycyclohexanone oxime (I) by contacting with a chlorinating agent as indicated in the following equation:

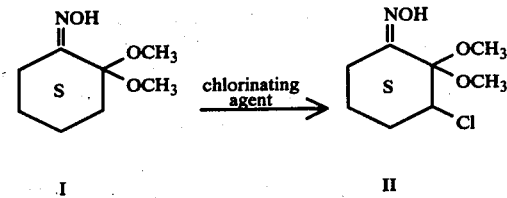

where the chlorinating agent is preferably elemental chlorine and the process is performed in a halogenated alkane solvent, such as methylene chloride or dichloroethane, at a temperature of about 25° to 35° C., in the presence of an active catalyst such as anhydrous hydrogen chloride, and the obtained yield of the 3-chloro product is in the range of 90 to 95% of theory. The utility of the product is described in U.S. Pat. No. 3,928,445, wherein the product can be subsequently subjected successively to the known organic reactions of Beckmann cleavage, reductive amination, resolution and hydrolysis to yield L-lysine hydrochloride, an essential amino acid in the human diet.

Included among the ketoximes of formula A which are applicable in the instant invention are those containing β,β-dialkoxy groups where the alkyl radicals X and Y of the alkoxy groups are independently selected from linear or branched alkyl groups containing 1 to 4 carbon atoms and are designated as $C_1$-$C_4$ alkyl and include methyl, ethyl, propyl, butyl, isopropyl and sec-butyl. The methyl radical is preferred and it is also preferred to use two radicals that are identical. The radicals R and R' are independently selected from linear or branched alkyl groups containing at least one carbon atom and include methyl, ethyl, propyl, isopropyl, butyl, t-butyl, hexyl, decyl, dodecyl, octadecyl and higher alkyl radicals. Here, selection of the size of the particular R and R' groups is not restrictive above the limitation of at least one carbon atom, since the process is general and the only proviso being that the ketoximes be soluble in the solvent described in the invention. It is preferred to use alkyl radicals R and R' that are linear or branched and contain 1 to 18 carbon atoms designated $C_1$-$C_{18}$, and it is particularly preferred to use alkyl radicals that are linear or branched and contain 1 to 8 carbon atoms, designated as $C_1$-$C_8$. The radicals R and R' can be the same or different.

Included among the ketoximes of formula B which are applicable in the invention are those containing β,β-dialkoxy groups where the alkyl radicals X and Y of the alkoxy groups are the same as described above in formula A.

The methylene chain $(CH_2)_n$ in the formula B has integer values of n of at least 2 and includes integer values of 2 to 9 and higher. Representative examples of cycloalkyl ketoximes of formula B that are applicable in the invention include 2,2-dialkoxy derivatives of cyclopentanone, cyclohexanone, cycloheptanone, cyclooctanone, cyclononanone, cyclodecanone, cycloundecanone, and cyclododecanone oximes. The 2,2-dialkoxycyclohexanone oximes, however, are preferred for both chlorination and bromination.

The methylene chain, $(CH_2)_n$, may also contain one or more $C_1$-$C_4$ alkyl substituents, being linear or branched, including methyl, ethyl, propyl, isopropyl, n-butyl and t-butyl on any of the carbon atoms of the methylene chain, but not in the β-position of the molecule. It is preferred to use a cycloalkyl compound of formula B that is unsubstituted by alkyl groups in the methylene $(CH_2)_n$ chain. However, although more than one alkyl substituent is applicable, it is preferred to have one alkyl substituent on the methylene chain.

The process of the invention generally involves dissolving a ketoxime of formulas A or B in an inert organic solvent and treating the ketoxime with a chlorinating or brominating agent, in a ratio of about 0.05 to 1.5 mols of chlorinating or brominating agent per mole of ketoxime, in the presence of an acid catalyst, at a temperature above 0° C.

Chlorinating and brominating agents which are useful in the reaction include elemental chlorine, elemental bromine, sulfuryl chloride, N-chloro- and N-bromosuccinimide and the like. The chlorinating or brominating agent is generally used in a molar ratio of about 0.05 to 1.5 moles of agent per mole of ketoxime and it is preferred to use a 1 to 1 molar ratio of chlorinating or brominating agent to ketoxime. If the brominating or chlorinating agent is in a gaseous form it can be bubbled into the solution of ketoxime and acid catalyst to contact the ketoxime, whereas if it is in a liquid form it can be added by means of a suitable addition vessel to contact the ketoxime. It is preferred to use elemental chlorine as the chlorinating agent and it is preferred to use elemental bromine as the brominating agent.

The acid catalyst in the invention can be any strong acid which will protonate the ketoxime in solution and can be either an inorganic mineral acid or an organic acid with the proviso that the acid catalyst be anhydrous under the process conditions. Representative examples of anhydrous inorganic acids which are useful in the invention include hydrogen chloride, hydrogen fluoride, hydrogen bromide, sulfuric acid and phosphoric acid. Representative examples of anhydrous organic acids include trifluoroacetic acid, p-toluenesulfonic acid, p-chlorobenzenesulfonic acid and methanesulfonic acid. Other types of acid catalysts which may be employed are SK 500 molecular sieves and acid ion exchange resins. It is preferred to use an inorganic mineral acid in the invention, as an acid catalyst, and it is particularly preferred to use anhydrous hydrogen chloride.

The acid catalyst can be supplied separately to the process or it can be introduced as the acid salt of the ketoxime used, as for example the hydrochloride salt of 2,2-dimethoxycyclohexanone oxime.

The amount of said catalyst used is about 0.001 to 1.5 moles per mole of ketoxime, and it is preferred to use 0.01 to 1 mole of catalyst per mole of ketoxime.

The process can also be conducted in some cases in the absence of any initial acid catalyst present due to the fact that the brominating or chlorinating agent will interact with the ketoxime to produce an acid product which serves to catalyze the reaction. However, it is preferred to use an acid catalyst to insure the fact that complete reaction occurs in the highest yield of product.

Solvents which are applicable in the invention include inert organic solvents containing 1 to 7 carbon atoms and which have good solubility for the ketoximes in the process. Preferred are solvents selected from the group consisting of halogenated alkanes, halogenated alkenes, halogenated aromatic hydrocarbons, aromatic hydrocarbons, dialkyl ethers and cycloalkyl ethers, or mixtures thereof.

The halogenated alkanes, alkenes and aromatic hydrocarbons may contain 1 to 4 halogen atoms such as fluorine, chlorine, bromine and iodine, or mixtures thereof, with the limitation that the halogenated solvent be inert under the reaction conditions and must not interact with the chlorinating or brominating agent used in the process. It is preferred to use chlorinated alkanes, alkenes and aromatic hydrocarbons. Representative examples of useful solvents include chloroform, carbon tetrachloride, methylene chloride, 1,2-dichloroethane, tetrachloroethane, chlorobutane, 1,2- and 1,4-dichlorobutane, chlorohexane, 1,2-dibromoethane, perchloroethylene, chlorobenzene, orthodichlorobenzene, bromobenzene, p-chlorotoluene, benzene, toluene, diethyl ether, dipropyl ether, tetrahydrofuran and dioxane.

The amount of solvent used is generally about 0.5 to 100 parts by weight of solvent per part of ketoxime and preferably about 10 to 1 parts by weight of solvent per part of ketoxime.

The process can be conducted in the open or under an inert atmosphere such as nitrogen. It is preferred to use an inert atmosphere free from moisture to prevent the introduction of moisture from the atmosphere into the process causing the formation of undesirable side-products. It is preferred to use a nitrogen atmosphere, protected from moisture in the process.

The temperature of the process is generally conducted in the temperature range of 0° C. to reflux temperature of the solvent, which may be 100° C. or higher, and it is generally preferred to conduct the process in a temperature range of about 20° to 50° C.

The time required for high yield in the process is generally about 0.1 to 2 hrs and generally a time of about 0.5 hrs is sufficient to obtain a satisfactory yield of chlorinated or brominated derivative.

Generally yields of about 70 to 95% of theory based on starting ketoxime are achieved by the process of this invention.

The following examples should not be construed to be limitations on the scope or spirit of the instant invention. Parts are by weight unless otherwise stated.

EXAMPLE 1

To a solution of 8.6 parts 2,2-dimethoxycyclohexanone oxime, in 68 parts of dry methylene chloride under a nitrogen atmosphere, were added about 5 parts anhydrous HCl and then about 4 parts of elemental chlorine by bubbling the gas into the solution, slowly over about a ½ hour period. The reaction was exothermic during the chlorine addition and the temperature was maintained between 20° to 30° C. by the use of a water bath. After the addition of elemental chlorine was complete, stirring of the mixture was continued at room temperature for about 2½ hours. A precipitate, formed during the reaction, was isolated and shown to be by-product hydrochloride of 2-oximino-1-methoxycyclohexene. The reaction mixture was washed with aqueous sodium bicarbonate, then twice with 50 parts of water, until the pH of the aqueous washes was finally about 6 to 7. The organic solvent was distilled from the solution under reduced pressure, yielding after drying, 6.9 parts of a brown solid with an impure melting point of about 135° to 140° C. The solid was purified by recrystallizing from ethyl ether, yielding a white solid with a melting point of 129° to 130° C. Elemental analysis and nuclear magnetic spectroscopy (NMR), including both proton and $C^{13}$ NMR spectroscopy, indicated that the purified solid was 3-chloro-2-2-dimethoxycyclohexanone oxime. Percent yield of 3-chloro-2,-2-dimethoxycyclohexanone oxime was 85% of theory based on starting 2,2-dimethoxycyclohexanone oxime.

EXAMPLE 2

Following the general procedure of Example 1, about 7.5 parts of elemental chlorine were added over a 2½ hour period to a solution of 17.3 parts of 2,2-dimethoxycyclohexanone oxime and a catalytic amount of anhydrous hydrogen chloride dissolved in about 85 parts dry methylene chloride. The reaction contents were maintained at a temperature of about 25° to 35° C. under a dry nitrogen atmosphere. After the addition was completed, the contents were allowed to stir for an additional half hour and were then treated by the procedure as described in Example 1. There was obtained 19.9 parts (90% of theory) of product 3-chloro-2,2-dimethoxycyclohexanone oxime as determined by nuclear magnetic resonance spectroscopy.

EXAMPLE 3

The general procedure of Example 1 was repeated except that ethylene dichloride was used as a solvent in place of methylene chloride, and the process was conducted at a temperature of about 50° C. rather than 25° to 35° C. There was obtained a yield higher than 90% of theory of product 3-chloro-2,2-dimethoxycyclohexanone oxime.

EXAMPLE 4

This example illustrates the use of sulfuryl chloride as a chlorinating agent. The general procedure of Example 1 was followed except that sulfuryl chloride was used in place of chlorine gas.

A solution of 1.66 parts sulfuryl chloride dissolved in 8 parts dry methylene chloride was added under a dry nitrogen atmosphere over a 15-minute period to a stirred solution of 1.73 parts 2,2-dimethoxycyclohexanone oxime dissolved in about 8 parts dry methylene chloride. After the addition was completed, the contents were stirred for an additional hour and then treated by the procedure in Example 1 to yield 1.5 parts of 3-chloro-2,2-dimethoxycyclohexanone oxime.

EXAMPLE 5

This example illustrates the chlorination of a 2,2-dialkoxycyclooctanone oxime.

Following the general procedure of Example 1, to a solution of 5.025 parts of 2,2-dimethoxycyclooctanone oxime in 40 parts dry methylene chloride at about 35° C., was added 1.78 parts elemental chlorine over about ¾ of an hour. The contents were stirred at 25° to 30° C. for about 2½ hours after the addition. The contents were then treated according to the procedure of Example 1 to yield 5.3 parts of product 3-chloro-2,2-dimethoxycyclooctanone oxime as determined by elemental analysis and nuclear magnetic resonance spectroscopy.

EXAMPLE 6

This example illustrates the chlorination of a 2,2-didimethoxycyclohexanone oxime substituted in the $(CH_2)_n$ methylene chain with an alkyl group.

Following the general procedure of Example 1, to a solution of 4.58 parts of 5-t-butyl-2,2-dimethoxycyclohexanone oxime in 20 parts dry methylene chloride, under a dry nitrogen atmosphere, was added about 1.5 parts elemental chlorine at about 25° to 35° C. over about ¾ of an hour. After the addition, the contents were stirred for an additional hour and then treated according to the procedure of Example 1 yielding 4.6 parts of 5-t-butyl-3-chloro-2,2-dimethoxycyclohexanone oxime as determined by elemental analysis and nuclear magnetic resonance spectroscopy.

EXAMPLE 7

This example illustrates the bromination of a 2,2-dialkoxycyclohexanone oxime.

Following the general procedure of Example 1, but using bromine in place of chlorine, to a solution of 8.65 parts of 2,2-dimethoxycyclohexanone oxime dissolved in 35 parts dry methylene chloride, at temperature between 0° to 5° C., was added about 2 parts of anhydrous hydrogen chloride. The contents were warmed to room temperature and 8.5 parts of bromine dissolved in 8 parts of dry methylene chloride were added over about a 15-minute period. The contents were allowed to stir for 1 hour at room temperature after the addition. The contents were then treated, according to the procedure of Example 1 yielding 11.8 parts of 3-bromo-2,2-dimethoxycyclohexanone oxime as determined by nuclear magnetic resonance spectroscopy.

EXAMPLE 8

This example illustrates the bromination of a 2,2-dialkoxycyclooctanone oxime.

Following the general procedure of Example 1, but using diethyl ether as a solvent in place of methylane chloride, to a solution of 5.025 parts of 2,2-dimethoxycyclooctanone oxime in 28 parts of diethyl ether was added 1.7 parts anhydrous hydrogen chloride at about 32° C. The mixture was stirred and to this was added about 4 parts bromine dissolved in 7 parts diethyl ether over a 5 minute period. After the addition the mixture was allowed to stir for about 0.5 hour. The mixture was then treated with aqueous sodium carbonate to remove dissolved acids in the ether layer and then worked with water. The ether phase was then dried and then distilled under vacuum to yield 50 percent of theory of 3-bromo-2,2-dimethoxycyclooctanone oxime as determined by nuclear magnetic resonance spectroscopy.

EXAMPLE 9

This example illustrates the chlorination of a dialkoxyalkyl ketoxime of formula (A).

Following the general procedure of Example 1, to a solution of 4.73 parts of 4,4-dimethoxy-3-oximinoheptane and 0.2 parts anhydrous hydrogen chloride dissolved in 20 parts dry methylene chloride, at 30 to 35° C., under a dry nitrogen atmosphere, was added 1.8 parts of elemental chlorine over a ½-hour period. After the addition, the contents were stirred for ½-hour and then treated according to the procedure in Example 1 to yield 3.5 parts of 5-chloro-4,4-dimethoxy-3-oximinoheptane as determined by nuclear magnetic resonance spectroscopy.

EXAMPLE 10

This example illustrates the bromination of a dialkoxyalkyl ketoxime of formula (A).

Following the general procedure of Example 1, but using bromine in place of chlorine, to a solution of 4.73 parts of 4,4-dimethoxy-3-oximinoheptane and 0.1 parts anhydrous hydrogen chloride in 20 parts of dry methylene chloride were added about 4 parts bromine dissolved in 8 parts dry methylene chloride over a 1 hour period at a temperature of 25° to 35° C. under a dry nitrogen atmosphere. After the addition was completed, the contents were stirred and treated according to the procedure of Example 1 yielding 5-bromo-4,4-dimethoxy-3-oximinoheptane as determined by nuclear magnetic resonance spectroscopy.

We claim:

1. Process for mono-brominating or monochlorinating an α,α-dialkoxyalkyl or α,α-dialkoxycycloalkyl ketoxime in the β-position comprising contacting a solution of such ketoxime, selected from the following formulae:

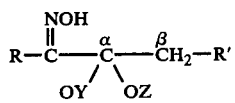

(A)

where Y and Z of the alkoxy groups are independently selected from linear or branched $C_1$–$C_4$ alkyl; and R and R' are independently selected from linear or branched alkyl containing one to eighteen carbon atoms; or

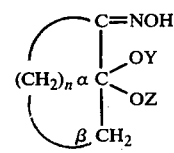

(B)

where Y and Z of the alkoxy groups are independently selected from linear or branched $C_1$–$C_4$ alkyl, and n is an integer from 2 to 9; or such compound substituted in the methylene $(CH_2)_n$ chain by at least one linear or branched $C_1$–$C_4$ alkyl radical; in an inert organic solvent with a chlorinating or brominating agent in a ratio of about 0.05 to 1.5 moles of chlorinating or brominating agent per mole of said ketoxime, in the presence of an acid catalyst, at a temperature above 0° C.

2. The process of claim 1 wherein the α,α-dialkoxycycloalkyl ketoxime is 2,2-dimethoxycyclohexanone oxime contacted with a chlorinating agent to produce 3-chloro-2,2-methoxycyclohexanone oxime.

3. The process of claim 1 wherein the organic solvent contains 1 to 7 carbon atoms and is selected from the group consisting of halogenated alkanes, halogenated alkenes, halogenated aromatic hydrocarbons, aromatic hydrocarbons, dialkyl ethers, cycloalkyl ethers or mixtures thereof.

4. The process of claim 3 wherein the organic solvent is a halogenated alkane containing 1 to 4 halogen atoms.

5. The process of claim 4 wherein the halogenated alkane is methylene chloride or dichloroethane.

6. The process of claim 1 wherein the chlorinating or brominating agent is sulfuryl chloride, N-bromo- or N-chlorosuccinimide, elemental bromine or elemental chlorine.

7. The process of claim 6 wherein the chlorinating agent is elemental chlorine.

8. The process of claim 1 wherein the acid catalyst is an anhydrous inorganic acid or organic acid.

9. The process of claim 8 wherein the acid catalyst is hydrochloric acid.

10. The process of claim 1 wherein the acid catalyst is employed in an amount of 0.001 to 1 mole per mole of ketoxime.

11. The process of claim 1 wherein the brominating or chlorinating agent is employed in an amount of about 0.1 to 1.5 moles per mole of ketoxime.

12. The process of claim 1 wherein the organic solvent is employed in an amount of about 10 to 1 parts by weight per part of ketoxime.

13. The process of claim 1 conducted at a temperature from 0° C. to about 70° C.

* * * * *